May 2, 1972 W. A. WARRINER Plant Pat. 3,144
ROSE PLANT
Filed Sept. 9, 1970
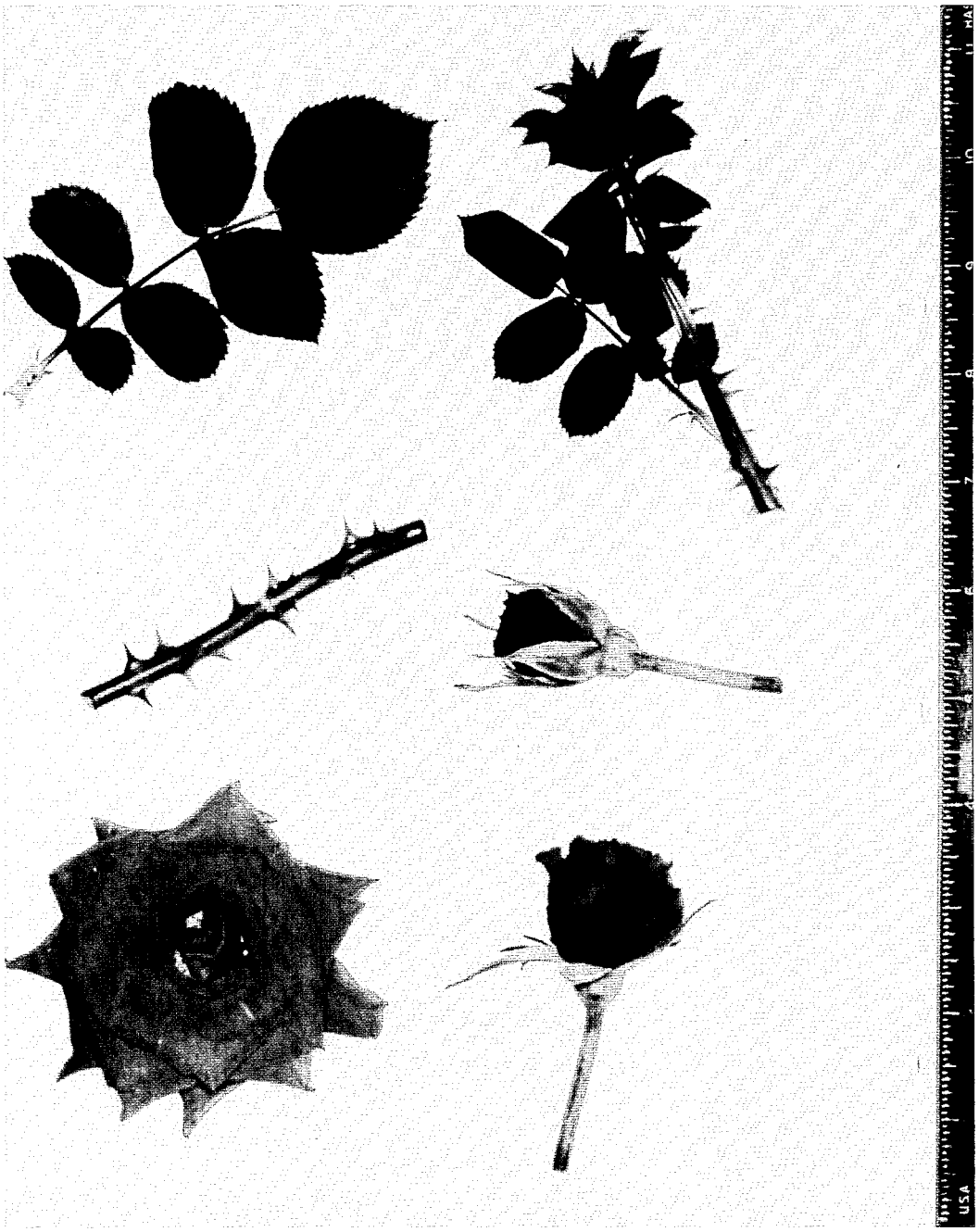
WILLIAM A. WARRINER
INVENTOR
BY
BUCKHORN, BLORE, KLARQUIST & SPARKMAN
ATTORNEYS

United States Patent Office

Plant Pat. 3,144
Patented May 2, 1972

3,144
ROSE PLANT

William A. Warriner, Tustin, Calif., assignor to Jackson & Perkins Company, Medford, Oreg.

Filed Sept. 9, 1970, Ser. No. 70,943
Int. Cl. A01h *5/00*
U.S. Cl. Plt.—28 1 Claim

The present invention relates to a new and distinct variety of rose plant of the floribunda class originated by crossing two unnamed seedlings.

The primary objective of this breeding was to produce a new and improved variety of the floribunda class bearing long lasting, non-blueing, well formed red flowers in quantities suitable for greenhouse production of cut blooms.

This objective was fully achieved, along with other desirable improvements as evidenced by the following unique combination of characteristics which are outstanding in the new variety, and which distinguish it from its parents, as well as from all other rose varieties of which I am aware:

(1) A vigorous and angular branching habit of growth.
(2) An unusually pronounced resistance to effects of rose powdery mildew as observed under greenhouse and garden conditions at Irvine, Calif.
(3) A unique persistence in flower color, showing very little change, after several days, from Currant Red (Wilson).
(4) Stiff, strong flower petals lasting on the flower for 7 to 10 days under normal, comfortable living conditions.

Asexual reproduction of my new variety by budding, as performed at Wasco, Calif., shows that the aforementioned characteristics and distinctions propagate true to form through succeeding propagation.

The accompanying illustration shows typical specimens of the vegetative growth and flowers of my new variety in different stages of development, depicted in color as nearly true as it is reasonably possible to make the same in a color illustration.

The following is a detailed description of my new variety, with color terminology in accordance with either Ridgway's "Color Standards and Nomenclature" (R), or Wilson's "Horticultural Color Chart" (W), except where ordinary dictionary significance of color is indicated.

Parentage: Seedling.
- *Seed parent.*—An unnamed seedling of "Independence"×"Siren."
- *Pollen parent.*—An unnamed seedling of unnamed parents.

Classification:
- *Botanic.*—Rosa hybrid.
- *Commercial.*—Floribunda.

*Flower*

(Observations made at Irvine, Calif., in early part of month of June in morning of flowers from plants in greenhouse.)

Blooming habit: Recurrent—Continuous.

Bud:
- *Size.*—Medium (¾"–1").
- *Form.*—Pointed, ovoid.
- *Color.*—When sepals first divide—Maroon, Plate 1 (R). When half blown—inside of petals; Currant Red 821(W)—appears brighter when pubescence reflects greatest amount of light; base of petals Straw Yellow 604 (W)—occasionally white midrib on outer petals; reverse of petals—Currant Red 821 (W) except for very small crescent at base of petals—Straw Yellow 604/2 (W), white midrib does not show on reverse side.

- *Sepals.*—Color—Inside: Absinthe Green, Plate 31 (R), outer edges shaded with Rainette Green, Plate 31 i (R) with little Tomentum, Plate 31 i (R). Outside: Absinthe Green, Plate 31 (R), outer edges are shaded with Rainette Green, Plate 31 i (R). Three appendaged sepals lightly appendaged. Two unappendaged sepals smooth edged.
- *Receptacle.*—Color—Bice Green, Plate 17, k (R). Shape—cylindrical with rounded bottom or base; size—large, broad; surface—smooth.
- *Peduncle.*—Length—medium; surface—very small prickles; color—Bice Green, Plate 17 k (R); strength—Stiff, erect.
- *Opening.*—Petal edges roll under lightly giving a buntly pointed shape to petals.

Bloom:
- *Size.*—Large (3"–3½").
- *Borne.*—Singly and in irregular clusters of 3–4 flowers.
- *Stems.*—Long, strong.
- *Form.*—When first open—high center. Permanence—retains its form to the end.
- *Petalage.*—Number of petals under normal conditions from 23 to 35 with 3–4 petaloids.
- *Color.*—Center of flower—upper side of petals—Currant Red, 821 (W). Reverse side of petals—Cardinal Red 822/1 (W). Outer petals—upper side of petals—same as center petals. Reverse of petals—same as center petals. Base of petals—small circular area similar to Empire Yellow, 603/1 (W). General tonality from a distance—Currant Red, 821 (W). No Variegations.
- *Discoloration.*—General tonality at end of first day—lightens very little. Third day—lightens to Currant Red 821/3 (W).
- *Fragrance.*—None.

Petals:
- *Texture.*—Leathery.
- *Surface.*—Inside—satiny. Reverse—satiny.
- *Shape.*—Round.
- *Form.*—Edges slightly quilled.
- *Arrangement.*—Imbricated.
- *Petaloids in center.*—Few.
- *Persistence.*—Drop off cleanly.
- *Lastingness.*—On the plant—very long. As cut flower—very long.

Reproductive parts:
- *Stamens, anthers.*—Medium, many; regularly arranged around styles. Color—yellow.
- *Stamens, filaments (threads).*—Medium. Color—white.
- *Pollen.*—Color—gold yellow.
- *Styles.*—Loosely separated, of even length.
- *Stigmas.*—Color—white.
- *Ovaries.*—All enclosed in calyx.

*Plant*

Form: Bush.

Growth: Very vigorous; upright; branching.

Foliage: Compound of 3 to 5 leaflets.
- *Size.*—Large.
- *Quantity.*—Normal.
- *Color.*—New foliage—Hay's Maroon, Plate 13, 1 'm (R). Old foliage—Empire Green, Plate 32. 33" m (R).
- *Leaflets.*—Shape—nearly elliptical. Texture—Upper side—leathery. Under side—smooth, veins raised. Ribs and veins—prominent. Edge—Serrated. Serration—Single; small. Petiole—Rachis—Color—reddish. Small prickles on upper ridges of rachis. Underside—prickles. Stipules—Short. Disease resistant—Resistant to mildew and blackspot under normal growing conditions at Irvine, Calif.

Wood:

*New wood.*—Color—Chromium green, Plate 32, 31" i (R). Bark—Smooth.

*Old wood.*—Color—Same as new wood. Bark—smooth with many small prickles.

Thorns:

*Quantity.*—On main stalks from base—ordinary. On laterals from stalk—ordinary.

*Form.*—Broad base; long; straight and angles downward.

*Color when young.*—Brown.

*Position.*—Irregular.

*Prickles.*—Quantity—On main stalks—many; on laterals—many. Color—Brown.

*Short needles.*—Quantity—On main stalks—few.

I claim:

1. A new and distinct variety of rose plant of the floribunda class substantially as herein shown and described, characterized particularly as to novelty by the unique combination of a vigorous, angularly branched habit of growth, an ovoid, pointed bud of maroon color, a uniformly imbricated flower form, the color of the open flower is Currant Red on the upper side of the petals and Cardinal Red on the reverse side, and an unusually pronounced resistance to powdery mildew, wherever this varity has been observed, is also a distinguishing characteristic.

No references cited.

ROBERT E. BAGWILL, Primary Examiner